United States Patent [19]

Gross

[11] Patent Number: 4,900,478
[45] Date of Patent: Feb. 13, 1990

[54] NOVEL RETINOIDS

[75] Inventor: Günter Gross, Weil a/Rhein, Fed. Rep. of Germany

[73] Assignee: Hoffmann-La Roche Inc., Nutley, N.J.

[21] Appl. No.: 102,935

[22] Filed: Sep. 30, 1987

[30] Foreign Application Priority Data

Oct. 6, 1986 [CH] Switzerland .................. 3987/86
Aug. 21, 1987 [CH] Switzerland .................. 3216/87

[51] Int. Cl.$^4$ ............................ C11C 3/00; C11C 3/12
[52] U.S. Cl. .................. 260/408; 260/404.5; 260/410.9 V
[58] Field of Search .................. 260/405.5, 410.9, 408

[56] References Cited

U.S. PATENT DOCUMENTS

| 4,054,589 | 10/1977 | Bollag et al. | 260/410.9 R |
|---|---|---|---|
| 4,169,103 | 9/1979 | Haenni et al. | 260/410.9 V |
| 4,215,215 | 7/1980 | Bollag et al. | 26/404.5 |
| 4,326,055 | 4/1982 | Loeliger | 542/429 |
| 4,476,056 | 10/1984 | Pawson | 260/410.9 |
| 4,677,120 | 6/1987 | Parish | 260/410.9 |
| 4,722,939 | 2/1988 | Loev et al. | 260/410.9 V |

FOREIGN PATENT DOCUMENTS

WO84/01573 4/1984 PCT Int'l Appl.
1543825 4/1979 United Kingdom.

Primary Examiner—Patrick P. Garvin
Assistant Examiner—E. D. Irzinski
Attorney, Agent, or Firm—George M. Gould; William H. Epstein; Julie M. Blackburn

[57] ABSTRACT

The novel compounds of the formula

Ret-OA    I wherein

Ret is the acyl residue of a retinoid carboxylic acid, A is a residue $(-CHR-CH_2O)_nR^1$, $(-CH_2)_mSR^1$, $(-CH_2)_mXR^2$, $(-CH_2)_m-Het$, $-N(R^2)_2$, $-C(R^4)_2OC(O)R^3$, $-CH_2-CH(OR^2)CH_2OR^2$ or $-CH(CH_2OR^2)_2$;

R is hydrogen or methyl, $R^1$ is hydrogen, $C_{1-6}$-alkyl or $C_{1-6}$-alkanoyl, $R^2$ is $C_{1-6}$-alkyl, $R^3$ is $C_{1-6}$-alkyl, $C_{1-6}$-alkoxy, di-$C_{1-6}$-alkylamino, phenyl, substituted phenyl, styryl or styryl or 2-benzoyl-phenoxy-$C_{1-6}$-alkyl substituted in the phenyl residue;

$R^4$ is hydrogen, $C_{1-6}$-alkyl or phenyl;

X is >SO or >SO$_2$,

Het is the residue of a N-heterocyclic ring, n is a whole number of 3-40 and m is a whole number of 1-4, with the proviso that $R^1$ is $C_{1-6}$-alkyl or $C_{1-6}$-alkanoyl when A is a $-CH_2SR^1$, can be used as medicaments, especially for the topical treatment of dermatological disorders. The novel compounds are obtainable e.g. by esterifying a retinoid carboxylic acid Ret-OH with an alcohol HA and, if desired, subsequently transforming reactive groups in the molecule.

27 Claims, No Drawings

NOVEL RETINOIDS

BACKGROUND OF THE INVENTION

The present invention is concerned with novel retinoids of the formula

Ret-OA  I wherein
Ret is the acyl residue of a retinoid carboxylic acid, A is a residue $(-CHR)-CH_2O)_nR^1$, $(-CH_2)_mSR^1$, $(-CH_2)_mXR^2$, $(-CH_2)_m-Het$, $-N(R^2)_2$, $-C(R^4)_2OC(O)R^3$, $-CH_2-CH(OR^2)CH_2OR^2$ or $-CH(CH_2OR^2)_2$;

R is hydrogen or methyl,
$R^1$ is hydrogen, $C_{1-6}$-alkyl or $C_{1-6}$-alkanoyl,
$R^2$ is $C_{1-6}$-alkyl,
$R^3$ is $C_{1-6}$-alkyl, $C_{1-6}$-alkoxy, di-$C_{1-6}$-alkylamino, phenyl, substituted phenyl, styryl or styryl or 2-benzoyl-phenoxy-$C_{1-6}$-alkyl substituted in the phenyl residue;
$R^4$ is hydrogen, $C_{1-6}$-alkyl or phenyl;
X is >SO or >SO$_2$,
Het is the residue of a N-heterocyclic ring,
n is a whole number of 3–40 and
m is a whole number of 1–4, with the proviso that $R^1$ is $C_{1-6}$-alkyl or $C_{1-6}$-alkanoyl when A is a $-CH_2SR^1$.

Under the term retinoid carboxylic acids there are to be understood hereinafter compounds which contain the nonatetraenoic acid residue present in retinoic acid or the carboxyphenyl-propen-2-yl residue derived therefrom by cyclization, which residues can also be substituted. Such retinoid carboxylic acids are described e.g. in U.S. Pat. Nos. 4 215 215, 4 054 589, 4 326 055 and 4 476 056. Of particular interest are retinoid carboxylic acids of the formulae

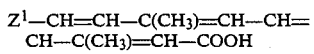  (a)

and

  (b)

in which $Z^1$ is a substituted phenyl or cyclohexenyl residue, $Z^2$ is a substituted bicyclic carbocyclic or heterocyclic residue and Ph is a phenylene residue and in which the double bonds in the polyene chain of (a) can have the E- or Z-configuration.

Examples of substituted phenyl residues $Z^1$ are phenyl residues which are substituted, preferably multiply, by $C_{1-6}$-alkyl, $C_{1-6}$-alkoxy, halogen or trifluoromethoxy. Examples of substituted cyclohexenyl residues are 2,6,6-trimethylcyclohexen-1-yl, 2,6,6-trimethyl-3-hydroxycyclohexen-1-yl and 2,6,6-trimethyl-3-oxo-cyclohexen-1-yl. Examples of substituted bicyclic carbocyclic residues are 1,1,3,3-tetramethyl-5-indanyl and 5,6,7,8-tetrahydro-5,5,8,8-tetramethyl-2-naphthyl. Examples of bicyclic heterocyclic residues are 4,4-dimethyl-6-chromanyl, 4,4-dimethyl-6-thiochromanyl, 4,4-dimethyl-1,2,3,4-tetrahydro-6-quinolinyl and 4,4-dimethyl-6-thiochromanyl 1,1-dioxide.

DETAILED DESCRIPTION

Preferred compounds of formula I are those in which Ret is the acyl residue of all-trans-9-(4-methoxy-2,3,6-trimethylphenyl)-3,7-dimethyl -2,4,6,8-nonatetraenoic acid, of p-[(E)-2-(5,6,7,8-tetrahydro-5,5,8,8-tetramethyl-2-naphthyl)propenyl]benzoic acid, of all-trans-vitamin-A acid or of 13-cis-vitamin-A acid.

Preferred residues A are those of the formula $-C(R^4)_2OC(O)R^3$, especially those in which $R^3$ is $C_{1-6}$-alkyl and $R^4$ is hydrogen or $C_{1-6}$-alkyl. Examples of $C_{1-6}$-alkyl and $C_{1-6}$-alkoxy are straight-chain and branched alkyl residues with 1–6 C-atoms such as methyl, ethyl, propyl, isopropyl, butyl, tert.-butyl, n-pentyl and n-hexyl. Where two residues $R^1$, $R^2$, or $R^4$ are present in A, these can be the same or can be different from each other. Examples of heterocyclic residues Het are 5–7-membered saturated or unsaturated monocyclic residues such as pyrrolidino, piperidino, mono- or diketo-pyrrolidino, mono- or diketo-piperidino, piperazino, $N^4$-$C_{1-4}$-alkylpiperazino, morpholino and thiamorpholino.

Substituted phenyl residues and styryl residues $R^3$ can contain one or more substitutents such as hydroxy, $C_{1-6}$-alkoxy and $C_{1-6}$-alkanoyloxy. Examples of such residues are hydroxyphenyl, 3,4,5-trimethoxyphenyl, acetoxyphenyl and methoxystyryl. A 2-benzoylphenoxy-$C_{1-6}$-alkyl residue can be substituted in the phenoxy part by $C_{1-6}$-alkyl, $C_{1-6}$-alkoxy or halogen.

The compounds of formula I can be manufactured in accordance with the invention by reacting a retinoid carboxylic acid of the formula Ret-OH or a reactive derivative thereof with an alcohol of the formula HA or a reactive derivative thereof or a halide of the formula Hal-A, whereby Ret and A have the significance given above and Hal is halogen, or reacting a compound of the formula Ret—O—C(R$^4$)$_2$—Hal with a carboxylic acid of formula R$^{31}$COOH, whereby Ret, Hal and R$^4$ have the significance given above and R$^{31}$ is $C_{1-6}$-alkyl, phenyl, substituted phenyl, styryl or styryl substituted in the phenyl residue, in the presence of a condensation agent and, if desired, functionally modifying reactive groups in the reaction product.

In one embodiment of the process in accordance with the invention a retinoid carboxylic acid of the formula Ret-OH is reacted with an alcohol of the formula HA in the presence of a condensation agent such as N,N-carbonyldiimidazole or N,N'-dicyclohexylcarbodiimide. The reaction is conveniently carried out in an inert organic solvent, e.g. an ether such as tetrahydrofuran or dioxan. The reaction temperature is not critical, and the reaction is conveniently carried out at room temperature. The reaction is preferably carried out under an inert gas and with the exclusion of light and moisture.

In another embodiment of the process in accordance with the invention a reactive derivative of a retinoid carboxylic acid Ret-OH, e.g. an acid halide or anhydride, preferably the acid chloride, can be reacted with an alcohol of the formula HA. Suitable condensation agents for this reaction are bases such as amines, e.g. triethylamine.

In a further embodiment of the process in accordance with the invention a retinoid carboxylic acid Ret-OH can be reacted with a reactive derivative of an alcohol HA. As examples of reactive derivatives there come into consideration e.g. tosylates and mesylates or halides, i.e. compounds in which one hydroxy group is replaced by a tosyloxy or mesyloxy group or by halogen, especially iodine. Finally, a haloalkyl ester of a retinoid carboxylic acid, i.e. a compound of the formula Ret—O—C(R$_4$)$_2$—Hal, can be reacted with a carboxylic acid of the formula R$^{31}$COOH. 1,8-Diazabicyclo(5,4,0)-undec-7-ene(1.5–5) is a preferred condensation agent for this reaction. A chloroalkyl ester, especially the chloromethyl ester, is the preferred haloalkyl ester and an alkanecarboxylic acid such as acetic acid is the preferred carboxylic acid of the formula $R^{31}COOH$. All of these reactions can be carried out in a manner known per se, e.g. as described in Tetrahedron, Vol. 36,2409-2433, 1980. In the previously described reactions there is preferably used an alcohol HA in which only one free hydroxy group is present and further hydroxy groups which may be present are present in protected form, for example as a readily cleavable ether such as the tetrahydropyranyl ether or as a readily cleavable ester. Such protecting groups can be cleaved off from the initially obtained reaction product of the alcohol HA with the retinoid carboxylic acid or their reactive derivatives in a manner known per se in order to obtain a compound of formula I.

The reaction products can be worked-up in a manner known per se, e.g. by distillation of the solvent, partition of the constituents of the residue between an organic solvent and an aqueous phase and chromatography, e.g. on silica gel, and/or crystallization from a solvent.

Reactive groups present in the reaction product of formula I can be functionally modified in a manner known per se.

For example, hydroxy groups and mercapto groups can be transformed by alkylation or acylation into $C_{1-6}$-alkoxy or $C_{1-6}$-alkanoyloxy or $C_{1-6}$-alkylthio or $C_{1-6}$-alkanoylthio groups, respectively. $C_{1-6}$-Alkylthio groups can be transformed by treatment with oxidation agents such as peracids into $C_{1-6}$-alkylsulphinyl and $C_{1-6}$-alkylsulphonyl groups.

The compounds of formula I are therapeutically active and can be used for the preferably topical treatment of disorders which are accompanied by cornification disorders of the skin such as e.g. psoriasis, ichthyosis and Darier's disease and in disorders of fibroblast activities such as e.g. keloidosis and localized sclerodermia; as well as in precanceroses of the skin and in acne.

The compounds are characterized, in particular, by a good tolerance, e.g. the absence of skin irritations in the case of topical administration. Methylene acetate (all-E)-9-(4-methoxy-2,3,6-trimethylphenyl)-3,7-dimethyl-2,4,6,8-nonatetraenoate is of particular interest.

The activity of the compounds can be determined in mice in which papillomas of the skin have been produced by treatment with dimethylbenzanthracene and croton oil. By the topical administration of compounds of formula I there is observed a regression of the papillomas which represents a measurement for the therapeutic efficacy of the compounds, e.g. for the treatment of psoiasis. The test methodology for the production of the papillomas is described in Europ. J. Cancer, Vol. 10, 731-737 (1974). The therapy of the skin papillomas is carried out when the mice have developed at least 6 papillomas with a minimum diameter of 5 mm. The compounds in a suitable vehicle are applied to each of 3 papillomas of groups each comprising 4 animals. In total 14 applications of in each case 2.5 μl of an active substance solution per papilloma take place, namely once daily on days 2, 3, 4, 5, 8, 9, 10, 11, 12, 15, 16, 17, 18 and 19. 4 animals serve as the control group to which only the vehicle is applied.

In order to evaluate the efficacy of the compounds, the sum of the diameter of the 3 treated papillomas is determined and the average value for each group is calculated. The measurements are carried out prior to the beginning of the therapy (day 1) and on days 8, 15 and 22. The increase or decrease of the average sum of the papilloma diameter per animal is expressed as a percentage of the starting value (day 1).

In these tests there was observed e.g. a regression of the treated papillomas of 90% with the application of the compound manufactured in Example 3 as a saturated solution in isopropyl myristate. In the case of the control animals in which the papillomas had been treated only with the vehicle (isopropyl myristate), practically no regression of the papilloma diameter became evident.

The compounds are characterized by a good penetration capability in the skin. In the case of in vitro tests with skin of nude rats there was observed e.g. with the compound of Example 3 a 200-fold greater penetration than in the case of the corresponding retinoid carboxylic acid (all-E-9-(4-methoxy-2,3,6-trimethylphenyl)-3,7-dimethyl-2,4,6,8-nonatetraenoic acid).

For topical use the active substances are conveniently used in the form of salves, tinctures, creams, gels, solutions, lotions, sprays, suspensions and the like. Salves and creams as well as solutions are preferred. These preparations specified for topical use can be manufactured by mixing the compounds of formula I as active ingredients with non-toxic, inert, solid or liquid carriers which are suitable for topical treatment and which are customary in such preparations.

For topical use there are conveniently suitable about 0.01-5%, preferably 0.05-1%, solutions and lotions as well as about 0.01-5%, preferably about 0.05-2%, salves or creams.

An antioxidant, e.g. tocopherol, N-methyl-γ-tocopheramine as well as butylated hydroxyanisole or butylated hydroxytoluene can be admixed with the preparations if desired. Furthermore, the preparations can contain other adjuvants and stabilizers, especially radiation protection agents such as silicates, talc, titanium dioxide, zinc oxide or cinnamic acid derivatives such as >Parsol<.

The following Examples illustrate the invention in more detail. The temperatures are given in degrees Celsius.

EXAMPLE 1

4.9 g of all-E-9-(4-methoxy-2,3,6-trimethylphenyl)-3,7-dimethyl-2,4,6,8-nonatetraenoic acid are suspended in 100 ml of dry tetrahydrofuran, treated with 2.9 g of N,N-carbonyldiimidazole and stirred for 4 hours while gassing with nitrogen and with the exclusion of light and moisture. In a second reaction flask 11.2 g of triethylene glycol in 40 ml of dry tetrahydrofuran are treated with 0.4 g of sodium hydride dispersion (55-60% in oil). After the hydrogen evolution has ended the two solutions are combined and stirred at room temperature for a further 4 hours. The solvent is then removed on a rotary evaporator in a vacuum, the oily residue is taken up in 300 ml of methylene chloride, extracted once with 150 ml of dilute hydrochloric acid solution and twice with 150 ml of saturated sodium chloride solution each time and the organic phase is dried over sodium sulphate. The oil remaining behind after filtration and evaporation is purified by means of chromatography over 250 g of silica gel with methylene chloride-tert.butyl methyl ether 7:3. The diester (melting point: 128°-129° from methylene chloride-petroleum ether) which results as a byproduct is separated as the first fraction. 2-(2-(Hydroxyethoxy)ethoxy)ethyl (all-E)-9-

(4-methoxy-2,3,6-trimethylphenyl)-3,7-dimethyl-2,4,6,8-nonatetraenoate is eluted as the main fraction. After evaporation of the eluate in a high vacuum there remains behind a yellow, waxy mass. Yield: 4.4 g, $R_F$ (silica gel/methylene chloride-tert.butyl methyl ether 7:3): 0.36.

EXAMPLE 2

In analogy to Example 1, from all-E-9-(4-methoxy-2,3,6-trimethylphenyl)-3,7-dimethyl-2,4,6,8-nonatetraenoic acid and tetraethylene glycol there is obtained, after working-up the reaction mixture (chromatography over silica gel with methylene chloride-tert.butyl methyl ether 7:3 as the elution agent), in addition to the diester, 2-(2-(2-(2-hydroxyethoxy)ethoxy)ethoxy)ethyl (all-E)-9-(4-methoxy-2,3,6-trimethylphenyl)-3,7-dimethyl-2,4,6,8-nonatetraenoate as a viscous oil. $R_F$ (silica gel/methylene chloride-tert.butyl methyl ether 7:3): 0.23.

EXAMPLE 3

The product of Example 2 can also be obtained by acylating the alcohol with the acid chloride. Thus, 16.3 g of all-E-9-(4-methoxy-2,3,6-trimethylphenyl)-3,7-dimethyl-2,4,6,8-nonatetraenoic acid are suspended in 200 ml of dry toluene and treated with 4.7 g of phosphorus trichloride. The reaction mixture is stirred at room temperature for 15 h while gassing with nitrogen and with the exclusion of light and moisture. The resulting acid chloride solution is added dropwise to a solution, cooled to 0° with ice, of 48 g of tetraethylene glycol and 13 g of triethylamine in 350 ml of methylene chloride. After the end of the addition the mixture is stirred at room temperature for a further 3 hours. The reaction solution is poured into 500 ml of saturated sodium chloride solution. The organic phase is separated, extracted twice with 200 ml of saturated sodium chloride solution each time and the organic phase is dried over sodium sulphate. In order to remove the acid which is still present, the yellow solution is filtered over 50 g of Florisil, concentrated in a vacuum and the residue is purified by chromatography over 350 g of silica gel with methylene chloride-tert.butyl methyl ether 7:3 as the eluent. The fractions which contain the product are combined and freed from solvent in a high vacuum. There remain behind 16.5 g of a yellow oil which is identical with the product of Example 2.

EXAMPLE 4

It is also possible to manufacture the ester of Example 2 by alkylating the acid with a tetraethylene glycol derivative in which one hydroxyl group is replaced by a reactive leaving group. Thus, 4.9 g of all-E-9-(4-methoxy-2,3,6-trimethylphenyl)-3,7-dimethyl-2,4,6,8-nonatetraenoic acid are suspended in 80 ml of dry acetonitrile and, after the addition 2.3 g of 1,8-diazabicyclo-(5,4,0)undec-7-ene(1.5-5), stirred at room temperature for 30 minutes while gassing with nitrogen and with the exclusion of light and moisture. 5.2 g of tetraethylene glycol monotosylate and 0.5 g of sodium iodide are then added and the mixture is stirred at room temperature for 15 hours. The solvent is evaporated in a vacuum, the residue is taken up in 250 ml of methylene chloride and extracted once with 100 ml of 2N hydrochloric acid and twice with 100 ml of saturated sodium chloride solution each time. The organic phase is dried over sodium sulphate and filtered over 50 g of Florisil in order to remove unreacted acid. The residue remaining behind after removing the solvent is chromatographed over 150 g of silica gel with methylene chloride-tert.butyl methyl ether (3:2) as the eluent. There can be isolated 4.2 g of a yellow oil which is identical with the product of Example 2.

The tetraethylene glycol monotosylate used as the starting material was prepared as follows:

A cold (0°) solution of 23.3 g of tetraethylene glycol and 19 g of pyridine in 100 ml of methylene chloride, is treated portionwise while stirring vigorously with a total of 19 g of p-toluenesulphonyl chloride. After completion of the addition the mixture is stirred at room temperature for a further 5 hours. 200 ml of methylene chloride and 100 ml of water are then added thereto and the organic phase is separated. The organic phase is washed successively with 100 ml of 2N hydrochloric acid, 100 ml of 5% sodium hydrogen carbonate solution and 100 ml of water and dried over sodium sulphate. The solvent is removed in a vacuum and the residue is chromatographed over 400 g of silica gel with methylene chloride-ethyl acetate-methanol (5:4:1) as the eluent. In addition to small amounts of tetraethylene glycol ditosylate there are isolated 17 g of tetraethylene glycol monotosylate as a colourless liquid. $R_F$ (silica gel/methylene chloride-ethyl acetate-methanol 5:4:1): 0.6.

EXAMPLE 5

In analogy to Example 1, from 3,7-dimethyl-9-(2,6,6-trimethyl-1-cyclohexen-1-yl)-2(Z),4,6,8(E)-nonatetraenoic acid and tetraethylene glycol there can be manufactured 2-(2-(2-(2-hydroxyethoxy)ethoxy)ethoxy)ethyl 3,7-dimethyl-9-(2,6,6-trimethyl-1-cyclohexen-1-yl)-2(Z),4,6,8(E)-nonatetraenoate. After chromatography over silica gel with methylene chloride-tert.butyl methyl ether (3:2) as the elution agent and evaporation of the solvent in a high vacuum the ester is obtained as a yellow, viscous oil. $R_F$ (silica gel/methylene chloride-tert.butyl methyl ether 3:2): 0.43.

EXAMPLE 6

In analogy to Example 1, from all-E-3,7-dimethyl-9-(2,6,6-trimethyl-1-cyclohexen-1-yl)-2,4,6,8-nonatetraenoic acid and tetraethylene glycol there is obtained, after chromatography of the reaction mixture (silica gel/methylene chloride-tert.butyl methyl ether 3:2), 2-(2-(2-(2-hydroxyethoxy)ethoxy)ethoxy)ethyl (all-E)-3,7-dimethyl-9-(2,6,6-trimethyl-1-cyclohexen-1-yl)-2,4,6,8-nonatetraenoate as a yellow, viscous oil. $R_F$ (silica gel/methylene chloride-tert.butyl methyl ether 3:2): 0.36.

EXAMPLE 7

In analogy to Example 1, from all-E-9-(4-methoxy-2,3,6-trimethylphenyl)-3,7-dimethyl-2,4,6,8-nonatetraenoic acid and polyethylene glycol 400 there can be manufactured polyethylene glycol(400) mono-(all-E)-9-(4-methoxy-2,3,6-trimethylphenyl)-3,7-dimethyl-2,4,6,8-nonatetraenoate. The reaction mixture is purified by chromatography over silica gel. In so doing, the diester which results in small amounts is firstly eluted with methylene chloride-ethyl acetate (1:1). The monoester can then be eluted with acetone-ethyl acetate (1:1). There is obtained a polyethylene glycol ester mixture with an average ethylene oxide number of 9. The product is a yellow, viscous liquid. $R_F$ (silica gel/ethyl acetate-acetone 1:1): 0.1–0.6 (several spots); $R_F$ (HPTLC-RP-18/methanol): 0.55.

EXAMPLE 8

In analogy to Example 1, from all-E-9-(4-methoxy-2,3,6-trimethylphenyl)-3,7-dimethyl-2,4,6,8-nonatetraenoic acid and polyethylene glycol 600 there can be manufactured polyethylene glycol(600) mono-(all-E)-9-(4-methoxy-2,3,6-trimethylphenyl)-3,7-dimethyl-2,4,6,8-nonatetraenoate. The reaction mixture is purified by chromatography over silica gel. Diester which also results in small amounts is firstly separated with ethyl acetate. The monoester can be eluted with ethyl acetate-acetone (1:2). After removing the solvent in a high vacuum there remains behind a yellow, viscous oil which is identified analytically as the polyethylene glycol ester mixture with an average ethylene oxide number of 13. $R_F$ (silica gel/ethyl acetate-acetone 1:2): 0.1–0.55 (several spots); $R_F$(HPTLC-RP-18/methanol): 0.57.

EXAMPLE 9

In analogy to Example 1, from all-E-9-(4-methoxy-2,3,6-trimethylphenyl)-3,7-dimethyl-2,4,6,8-nonatetraenoic acid and polyethylene glycol 1000 there is obtained polyethylene glycol(1000) mono-(all-E)-9-(4-methoxy-2,3,6-trimethylphenyl)-3,7-dimethyl-2,4,6,8-nonatetraenoate. The product is purified by chromatography over silica gel with methylene chloride-methanol 9:1 as the elution agent. After removing the solvent there is obtained a yellow wax of melting point 32°–34° which is identified as the polyethylene glycol ester mixture with an average ethylene oxide number of 22. $R_F$ (silica gel/methylene chloride-methanol 9:1): 0.5; $R_F$ (HPTLC-RP-18/methanol-water 9:1): 0.21.

EXAMPLE 10

In analogy to Example 1, from all-E-9-(4-methoxy-2,3,6-trimethylphenyl)-3,7-dimethyl-2,4,6,8-nonatetraenoic acid and 2-methylthio-ethanol there can be manufactured 2-(methylthio)ethyl (all-E)-9-(4-methoxy-2,3,6-trimethylphenyl)-3,7-dimethyl-2,4,6,8-nonatetraenoate. In order to isolate the product from the reaction mixture, it is extracted and chromatographed over silica gel with methylene chloride as the elution agent. Melting point: 104° (from methylene chloride-hexane), $R_F$ (silica gel/methylene chloride): 0.63.

EXAMPLE 11

An ice-cooled solution of 10 g of 2-(methylthio)ethyl (all-E)-9-(4-methoxy-2,3,6-trimethylphenyl)-3,7-dimethyl-2,4,6,8-nonatetraenoate (manufactured in Example 10) in 220 ml of methylene chloride is treated portionwise within 60 minutes with a total 4.5 g of 3-chloroperbenzoic acid. The reaction solution is stirred at 0° for a further 2 hours. A further 100 ml of methylene chloride are added thereto and the mixture is extracted twice with 100 ml of a 5% sodium hydrogen carbonate solution each time and twice with 100 ml of water each time. After filtration over 50 g of Florisil the evaporated residue is chromatographed over 250 g of silica gel with methylene chloride-tert.butyl methyl ether (2:3) as the elution agent. Fractions which contain the product are combined, evaporated in a vacuum and recrystallized from methylene chloride-hexane. There are obtained 5.1 g of 2-(methylsulphinyl)ethyl (all-E)-9-(4-methoxy-2,3,6-trimethylphenyl)-3,7-dimethyl-2,3,6,8-nonatetraenoate. Melting point: 109°–110°, $R_F$ (silica gel/methylene chloride-tert.butyl methyl ether 2:3): 0.17.

EXAMPLE 12

In analogy to Example 1, from all-E-9-(4-methoxy-2,3,6-trimethylphenyl)-3,7-dimethyl-2,4,6,8-nonatetraenoic acid and 2-hydroxyethyl methyl sulphone there is obtained 2-(methylsulphonyl)ethyl (all-E)-9-(4-methoxy-2,3,6-trimethylphenyl)-3,7-dimethyl-2,4,6,8-nonatetraenoate. After filtration over Florisil the product is recrystallized from methylene chloride-hexane. Melting point: 128°–129°, $R_F$(silica gel/methylene chloride-tert.butyl methyl ether 9:1): 0.74.

EXAMPLE 13

In analogy to Example 1, from all-E-9-(4-methoxy-2,3,6-trimethylphenyl)-3,7-dimethyl-2,4,6,8-nonatetraenoic acid and 1-(2-hydroxyethyl)-azacyclopentan-2-one there can be manufactured 2-(2-oxo-1-pyrrolidinyl)ethyl (all-E)-9-(4-methoxy-2,3,6-trimethylphenyl)-3,7-dimethyl-2,4,6,8-nonatetraenoate. The product can be isolated by chromatography over silica gel with methylene chloride-ethyl acetate (1:1). Melting point: 83°–84° (from methylene chloride-hexane), $R_F$ (methylene chloride-ethyl acetate 1:1): 0.35.

EXAMPLE 14

In analogy to Example 1, from (all-E)-3,7-dimethyl-9-(2,6,6-trimethyl-1-cyclohexen-1-yl)-2,4,6,8-nonatetraenoic acid and 1-(2-hydroxyethyl)-azacyclopentan-2-one there is obtained 2-(2-oxo-1-pyrrolidinyl)ethyl (all-E)-9-(2,6,6-trimethyl-1-cyclohexen-1-yl)-3,7-dimethyl-2,4,6,8-nonatetraenoate. After chromatography over silica gel with methylene chloride-ethyl acetate (7:3) and crystallization from methylene chloride-petroleum ether there are obtained yellow crystals of melting point 64°–66°. $R_F$ (silica gel/methylene chloride-ethyl acetate 7:3): 0.30.

EXAMPLE 15

Analogously to Example 1, from 3,7-dimethyl-9-(2,6,6-trimethyl-1-cyclohexen-1-yl)-2(Z),4,6,8(E)-nonatetraenoic acid and 1-(2-hydroxyethyl)-azacyclopentan-2-one there is obtained 2-(2-oxo-1-pyrrolidinyl)ethyl 3,7-dimethyl-9-(2,6,6-trimethyl-1-cyclohexen-1-yl)-2(Z),4,6,8(E)-nonatetraenoate. After chromatography over silica gel with methylene chloride-ethyl acetate (7:3) the product is recrystallized from methylene chloride-petroleum ether. Crystals with a melting point of 87°–89° are obtained. $R_F$ (silica gel/methylene chloride-ethyl acetate 7:3): 0.41.

EXAMPLE 16

In analogy to Example 1, from all-E-9-(4-methoxy-2,3,6-trimethylphenyl)-3,7-dimethyl-2,4,6,8-nonatetraenoic acid and 1-(2-hydroxyethyl)-succinimide there is manufactured 2-succinimidoethyl all-E-9-(4-methoxy-2,3,6-trimethylphenyl)-3,7-dimethyl-2,4,6,8-nonatetraenoate. In order to work-up the reaction mixture, it is, after extraction, chromatographed over silica gel with methylene chloride-ethyl acetate (4:1) and recrystallized from methylene chloride-hexane. Yellow crystals with a melting point of 127° are obtained. $R_F$ (silica gel/methylene chloride-ethyl acetate 4:1): 0.65.

EXAMPLE 17

In analogy to Example 1, from all-E-9-(4-methoxy-2,3,6-trimethylphenyl)-3,7-dimethyl-2,4,6,8-nonatetraenoic acid and 1-(2-hydroxyethyl)-glutarimide there is manufactured 2-glutarimidoethyl (all-E)-9-(4-methoxy- 2,3,6-trimethylphenyl)-3,7-dimethyl-2,4,6,8-nonatetraenoate. The product is isolated by chromatography over silca gel with methylene chloride-ethyl acetate (9:1) and crystallization from methylene chloride-hexane. Yellow crystals with a melting point of 127°–129° are obtained. $R_F$ (silica gel/methylene chloride-ethyl acetate 9:1): 0.5.

EXAMPLE 18

Analogously to Example 1, from all-E-9-(4-methoxy-2,3,6-trimethylphenyl)-3,7-dimethyl-2,4,6,8-nonatetraenoic acid and 1-(2-hydroxyethyl)-piperidine there is obtained 2-(1-piperidyl)ethyl (all-E)-9-(4-methoxy-2,3,6-trimethylphenyl)-3,7-dimethyl-2,4,6,8-nonatetraenoate. The ester is chromatographed over silica gel with methylene chloride-methanol (2:1) and recrystallized from petroleum ether. Melting point: 52°–53°. $R_F$ (silica gel/methylene chloride-methanol 2:1): 0.21.

EXAMPLE 19

In analogy to Example 1, from all-E-9-(4-methoxy-2,3,6-trimethylphenyl)-3,7-dimethyl-2,4,6,8-nonatetraenoic acid and 4-(2-hydroxyethyl)-morpholine there is manufactured 2-(4-morpholinyl)ethyl all-E-9-(4-methoxy-2,3,6-trimethylphenyl)-3,7-dimethyl-2,4,6,8-nonatetraenoate. The product is recrystallized from methylene chloride-hexane. Melting point: 93°, $R_F$ (silica gel/methylene chloride-tert.butyl methyl ether 4:1): 0.23.

EXAMPLE 20

In analogy to Example 1, from all-E-9-(4-methoxy-2,3,6-trimethylphenyl)-3,7-dimethyl-2,4,6,8-nonatetraenoic acid and N,N-diethyl-hydroxylamine there are manufactured N,N-diethyl-O-[(all-E)-9-(4-methoxy-2,3,6-trimethylphenyl)-3,7-dimethyl-2,4,6,8-nonatetraenoyl]hydroxylamine (melting point: 85°–86° from petroleum ether, $R_F$ (silica gel/cyclohexane-ethyl acetate 7:3): 0.44) and N,N-diethyl-O-9-[(2Z,4E,6E,8E) (4-methoxy-2,3,6-trimethylphenyl)-3,7-dimethyl-2,4,6,8-nonatetraenoyl]hydroxylamine (melting point: 138°–140° from petroleum ether, $R_F$ (silica gel/cyclohexane-ethyl acetate 7:3): 0.52). The two isomers are separated by chromatography over silica gel with methylene chloride-tert.butyl methyl ether 95:5.

EXAMPLE 21

1.6 g of 1,8-diazabicyclo(5,4,0)undec-7-ene(1.5-5) are added to a suspension of 3.2 g of all-E-9-(4-methoxy-2,3,6-trimethylphenyl)-3,7-dimethyl-2,4,6,8-nonatetraenoic acid in 70 ml of dry acetonitrile and the mixture is stirred at room temperature for 1 hour while gassing with nitrogen and with the exclusion of light and moisture. 3 g of iodomethyl acetate in 40 ml of acetonitrile are then added thereto and the mixture is stirred at room temperature for 15 hours. The solvent is removed in a vacuum, the residue is taken up in 200 ml of methylene chloride and washed once with 80 ml of 2N hydrochloric acid and twice with 100 ml of saturated sodium chloride solution each time. The organic phase is dried over sodium sulphate. In order to remove the unreacted acid, the organic phase is filtered over 40 g of Florisil, rinsed with methylene chloride-ether (1:1) and the filtrate is chromatographed over 150 g of silica gel with a total of 1.3 l of methylene chloride-hexane (3:1). The eluate is evaporated and the residual yellow oil is recrystallized from methylene chloride-petroleum ether. There are obtained 2.3 g of methylene acetate (all-E)-9-(4-methoxy-2,3,6-trimethylphenyl)-3,7-dimethyl-2,4,6,8-nonatetraenoate as orange-yellow crystals with a melting point of 78°–79°. $R_F$ (silica gel/hexane-methylene chloride-tert.butyl methyl ether 50:45:5): 0.59.

The iodomethyl acetate used as the starting material is prepared as follows:

21.7 g of chloromethyl acetate (prepared according to L. H. Ulich, R. Adams: J. Am. Chem. Soc. 43, 660–667 (1921)) and 45 g of sodium iodide in 200 ml of dry acetone are stirred at 40° for 2 hours. After cooling separated sodium chloride is removed, the filtrate is evaporated, the residue is taken up in 200 ml of methylene chloride and extracted twice with 100 ml of 5% sodium sulphite solution each time and twice with 100 ml of water each time. The organic phase is dried over sodium sulphate, the solvent is removed and the residue is distilled in a water-jet vacuum with exclusion of light and with the addition of a spatula tip of sodium sulphite. A colourless liquid of boiling point 49°–51°/13 mmHg is obtained.

EXAMPLE 22

In analogy to Example 21, from all-E-9-(4-methoxy-2,3,6-trimethylphenyl)-3,7-dimethyl-2,4,6,8-nonatetraenoic acid and iodomethyl pivalate there is obtained methylene (all-E)-9-(4-methoxy-2,3,6-trimethylphenyl)-3,7-dimethyl-2,4,6,8-nonatetraenoate pivalate. After crystallization from petroleum ether there are obtained yellow crystals with a melting point of 109°–111°. $R_F$ (silica gel/hexane-methylene chloride-tert.butyl methyl ether 50:45:5): 0.6.

EXAMPLE 23

Analogously to Example 21, from (all-E)-3,7-dimethyl-9-(2,6,6-trimethyl-1-cyclohexen-1-yl)-2,4,6,8-nonatetraenoic acid and iodomethyl pivalate there is manufactured methylene (all-E)-3,7-dimethyl-9-(2,6,6-trimethyl-1-cyclohexen-1-yl)-2,4,6,8-nonatetraenoate pivalate. After extraction of the reaction mixture the product is chromatographed over silica gel with methylene chloride-cyclohexane 1:1. After crystallization from methanol there are obtained yellow crystals with a melting point of 61°–62°. $R_F$ (silica gel/methylene chloride-cyclohexane 1:1): 0.42.

EXAMPLE 24

In analogy to Example 21, from all-E-9-(4-methoxy-2,3,6-trimethylphenyl)-3,7-dimethyl-2,4,6,8-nonatetraenoic acid and chloromethyl benzoate in the presence of sodium iodide there is obtained methylene benzoate. (all-E)-9-(4-methoxy-2,3,6-trimethylphenyl)-3,7-dimethyl-2,4,6,8-nonatetraenoate. In order to isolate the product from the reaction mixture it is, after extraction, chromatographed over silica gel with methylene chloride-hexane (7:3). After crystallization from methylene chloride-petroleum ether the ester is obtained as yellow crystals with a melting point of 136°–139°. $R_F$ (silica gel/hexane-methylene chloride-tert.butyl methyl ether 50:45:5): 0.74.

EXAMPLE 25

Analogously to Example 21, from all-E-9-(4-methoxy-2,3,6-trimethylphenyl)-3,7-dimethyl-2,4,6,8-nonatetraenoic acid and iodomethyl 3,4,5-trimethoxybenzoate there can be manufactured methylene (all-E)-9-(4-methoxy-2,3,6-trimethylphenyl)-3,7-dimethyl-2,4,6,8-nonatetraenoate-3,4,5-trimethoxybenzoate.

After extraction of the reaction mixture the organic phase is filtered over Florisil, rinsed with methylene chloride-ether (1:1) and concentrated in a vacuum. The residue crystallizes from ethyl acetate-petroleum ether with a melting point of 106°–108°. $R_F$ (silica gel/cyclohexane-ethyl acetate 7:3): 0.53.

The iodomethyl 3,4,5-trimethoxybenzoate used as the starting material is prepared in the following manner:

19 g of chloromethyl chlorosulphate in 30 ml of methylene chloride are introduced dropwise at room temperature into a stirred mixture of 21.1 g of 3,4,5-trimethoxybenzoic acid, 33.6 g of sodium hydrogen carbonate and 3.4 g of tetrabutylammonium hydrogen sulphate in 600 ml of methylene chloride-water (1:1). In order to complete the reaction, the mixture is stirred at room temperature for a further 2 hours, the two phases are then separated, the aqueous phase is washed with 100 ml of methylene chloride and the combined organic phases are dried over sodium sulphate. The solvent is removed in a vacuum and the residue is chromatographed over 450 g of silica gel with methylene chloride. Fractions containing the product are evaporated and the residue is crystallized from methylene chloride-petroleum ether. 10.5 g of chloromethyl 3,4,5-trimethoxybenzoate are obtained as colourless needles with a melting point of 85°–86°. $R_F$ (silica gel/methylene chloride): 0.45.

7.8 g of chloromethyl 3,4,5-trimethoxybenzoate are dissolved in 150 ml of acetonitrile, treated with 9 g of sodium iodide and stirred at room temperature for 15 hours whole gassing with nitrogen and with the exclusion of light. The separated sodium chloride is then filtered off and the filtrate is evaporated in a vacuum. The residue is taken up in 150 ml of ether, shaken with 100 ml of a 5% sodium sulphite solution and twice with 100 ml of water each time and the organic phase is dried over sodium sulphate. After filtering off the drying agent the ether is removed in a vacuum and the oily residue is used for the further reaction without additional purification. $R_F$ (silica gel/methylene chloride-petroleum ether 4:1): 0.45.

EXAMPLE 26

In analogy to Example 21, from all-E-9-(4-methoxy-2,3,6-trimethylphenyl)-3,7-dimethyl-2,4,6,8-nonatetraenoic acid and iodomethyl o-acetoxybenzoate there is manufactured methylene o-acetoxybenzoate (all-E)-9-(4-methoxy-2,3,6-trimethylphenyl)-3,7-dimethyl-2,4,6,8-nonatetraenoate. Melting point: 97°–98° (from ethyl acetate-petroleum ether), $R_F$ (silica gel/cyclohexane-ethyl acetate 7:3): 0.57.

The iodomethyl o-acetoxybenzoate used as the starting material was prepared from acetylsalicylic acid and chloromethyl chlorosulphate as described in Example 25 for chloromethyl 3,4,5-trimethoxybenzoate. The chloromethyl o-acetoxybenzoate (colourless liquid, $R_F$ (silica gel/methylene chloride): 0.68) is converted with sodium iodide into iodomethyl o-acetoxybenzoate (yellowish oil, $R_F$ (silica gel/methylene chloride): 0.7).

EXAMPLE 27

Analogously to Example 21, from all-E-9-(4-methoxy-2,3,6-trimethylphenyl)-3,7-dimethyl-2,4,6,8-nonatetraenoic acid and iodomethyl [(2-benzoyl-5-methoxy)phenoxy]acetate there can be manufactured methylene [(2-benzoyl-5-methoxy)phenoxy]acetate (all-E)-9-(4-methoxy-2,3,6-trimethylphenyl)-3,7-dimethyl-2,4,6,8-nonatetraenoate. In order to purify the reaction product, it is chromatographed over silica gel with methylene chloride-petroleum ether-tert.butyl methyl ether (26:10:1) and recrystallized from ethyl acetate-petroleum ether. Yellow crystals with a melting point of 119°–121° are obtained. $R_F$ (silica gel/methylene chloride-petroleum ether-tert.butyl methyl ether 26:10:1): 0.5.

The iodomethyl [(2-benzoyl-5-methoxy)phenoxyacetate used as the starting material is prepared from 2-(2-benzoyl-5-methoxy)phenoxy-acetic acid and chloromethyl chlorosulphate in analogy to the iodomethyl 3,4,5-trimethoxybenzoate of Example 25. The transformation of the chloromethyl [(2-benzoyl-5-methoxy)-phenoxy]acetate (colourless solid, melting point: 70°–72° from methylene chloride-petroleum ether) into iodomethyl [(2-benzoyl-5-methoxy)phenoxy]acetate is effected with sodium iodide in acetonitrile. $R_F$ (silica gel/methylene chloride): 0.44.

EXAMPLE 28

In analogy to Example 21, from all-E-9-(4-methoxy-2,3,6-trimethylphenyl)-3,7-dimethyl-2,4,6,8-nonatetraenoic acid and iodomethyl cinnamate there is manufactured methylene cinnamate (all-E)-9-(4-methoxy-2,3,6-trimethylphenyl)-3,7-dimethyl-2,4,6,8-nonatetraenoate. After crystallization from petroleum ether there are obtained yellow crystals with a melting point of 67°–69°. $R_F$ (silica gel/cyclohexane-ethyl acetate 7:3): 0.66.

The iodomethyl cinnamate used as the starting material is prepared from cinnamic acid and chloromethyl chlorosulphate as described in Example 25 for iodomethyl 3,4,5-trimethoxybenzoate. The chloromethyl cinnamate (yellowish liquid, $R_F$ (silica gel/methylene chloride-petroleum ether 4:1): 0.74) is transformed with sodium iodide into iodomethyl cinnamate. $R_F$ (silica gel/methylene chloride-petroleum ether 4:1): 0.78.

EXAMPLE 29

Analogously to Example 21, from all-E-9-(4-methoxy-2,3,6-trimethylphenyl)-3,7-dimethyl-2,4,6,8-nonatetraenoic acid and iodomethyl p-methoxycinnamate there is manufactured methylene p-methoxycinnamate (all-E)-9-(4-methoxy-2,3,6-trimethylphenyl)-3,7-dimethyl-2,4,6,8-nonatetraenoate. Melting point: 86°–88° (from ethanol). $R_F$ (silica gel/cyclohexane-ethyl acetate 8:2): 0.4.

The iodomethyl p-methoxycinnamate used as the starting product is prepared from p-methoxycinnamic acid and chloromethyl chlorosulphate in analogy to iodomethyl 3,4,5-trimethoxybenzoate of Example 25. The thus-obtained chloromethyl p-methoxycinnamate (colourless solid of melting point 64°–65° from ethyl acetate-petroleum ether) is transformed with sodium iodide in acetonitrile into iodomethyl p-methoxycinnamate. There is obtained a yellowish wax with $R_F$ (silica gel/cyclohexane-ethyl acetate 8:2): 0.52.

EXAMPLE 30

13.1 g of all-E-9-(4-methoxy-2,3,6-trimethylphenyl)-3,7-dimethyl-2,4,6,8-nonatetraenoic acid and 5.6 g of finely powdered potassium carbonate are stirred in 250 ml of dimethylformamide for 2 h at 80°. After adding 5.5 g of 1-chloroethyl acetate in 20 ml of dimethylformamide and 1 g of potassium iodide the reaction mixture is stirred for 18 h at 80°. Thereafter, the solvent is removed in a vacuum on a rotary evaporator, the residue is taken up in 300 ml of methylene chloride and extracted once with 150 ml of dilute hydrochloric acid solution and twice with 150 ml of saturated sodium chloride solution. The methylene chloride phase is dried over sodium sulphate and filtered over 80 g of Florisil. The Florisil is rinsed with methylene chloride-tert.butyl methyl ether 95:5. The yellow oil which remains behind after removing the solvent is purified by chromatography over 300 g of silica gel with methylene chloride/petroleum ether/tert.butyl methyl ether 30:65:5 as the elution agent. The pure fractions are combined, concentrated in a vacuum and the residue is crystallized. There are obtained 6.6 g of ethylidene acetate (all-E)-9-(4-methoxy-2,3,6-trimethylphenyl)-3,7-dimethyl-2,4,6,8-nonatetraenoate as yellow crystals with a melting point of 106°-108° (methylene chloride-petroleum ether). $R_F$ (silica gel/methylene chloride-petroleum ether-tert.butyl methyl ether 30:65:5)=0.34.

EXAMPLE 31

Analogously to Example 30, from all-E-9-(4-methoxy-2,3,6-trimethylphenyl)-3,7-dimethyl-2,4,6,8-nonatetraenoic acid and 1-chloroethyl benzoate there is obtained ethylidene benzoate (all-E)-9-(4-methoxy-2,3,6-trimethylphenyl)-3,7-dimethyl-2,4,6,8-nonatetraenoate. The purification, after extraction and Florisil filtration, is effected by two-fold crystallization from methylene chloride-methanol. There are obtained yellow crystals with a melting point of 123°-125°. $R_F$ (silica gel/methylene chloride-hexane-tert.butyl methyl ether 30:65:5)=0.4.

EXAMPLE 32

In analogy to Example 30, from all-E-9-(4-methoxy-2,3,6-trimethylphenyl)-3,7-dimethyl-2,4,6,8-nonatetraenoic acid and 1-chloroethyl ethyl carbonate in acetonitrile as the solvent there is manufactured ethylidene (ethyl carbonate) (all-E)-9-(4-methoxy-2,3,6-trimethylphenyl)-3,7-dimethyl-2,4,6,8-nonatetraenoate. After extraction and Florisil filtration the product is crystallized from acetone-methanol. There are obtained yellow crystals with a melting point of 117°-118°. $R_F$ (methylene chloride-petroleum ether 3:1)=0.71.

EXAMPLE 33

The product of example 21 can also be manufactured by alkylating acetic acid with the chloromethyl ester of retinoic acid. Thus, 0.16 g of acetic acid and 0.41 g of DBU (1,8-diazabicyclo(5,4,0)undec-7-ene(1.5-5)) in 20 ml of dry acetonitrile are stirred for 30 min. This solution is treated with 0.94 g of chloromethyl (all-E)-9-(4-methoxy-2,3,6-trimethylphenyl)-3,7-dimethyl-2,4,6,8-nonatetraenoate and the reaction mixture is stirred at 80° for 2 h with the exclusion of light and moisture. The solvent is removed on a rotary evaporator in a vacuum, the residue is taken up in 50 ml of methylene chloride and extracted with 25 ml of dilute hydrochloric acid solution and twice with 25 ml of saturated sodium chloride solution. The organic phase is dried over sodium sulphate and filtered over 15 g of Florisil. After evaporation of the solvent the residual oil is crystallized from 10 ml of ethanol. There is obtained 0.86 g of orange-yellow crystals with a melting point of 78°-80°, which are identical with the product from Example 21.

The chloromethyl (all-E)-9-(4-methoxy-2,3,6-trimethylphenyl)-3,7-dimethyl-2,4,6,8-nonatetraenoate used as the starting material was prepared in the following manner:

4.3 g of chloromethyl chlorosulphate in 25 ml of methylene chloride are added dropwise at room temperature to a stirred mixture of 6.5 g of all-E-9-(4-methoxy-2,3,6-trimethylphenyl)-3,7-dimethyl-2,4,6,8-nonatetraenoic acid, 0.68 g of tetrabutylammonium hydrogen sulphate and 6.7 g of sodium hydrogen carbonate in 80 ml of water/150 ml of methylene chloride. After the end of the addition the reaction mixture is stirred for a further 2 h. The phases are separated, the aqueous phase is again extracted with 50 ml of methylene chloride and the combined organic phases are dried over sodium sulphate. In order to remove unreacted starting material the organic phase is filtered over 50 g of Florisil which is rinsed with methylene chloride. After evaporation of the solvent the residual oil is chromatographed on 250 g of silica gel with methylene chloride-petroleum ether 1:1 as the eluent. The fractions containing the product are combined and freed from solvent in a vacuum. The oily residue is crystallized from methylene chloride/petroleum ether. There are obtained yellow crystals (5.3 g) with a melting point of 106°-108°. $R_F$ (silica gel/methylene chloride-petroleum ether 1:1)=0.38.

Example A (gel)

| Active substance | 0.05-1 g |
|---|---|
| Hydroxypropylcellulose | 2-5 g |
| Propylene glycol | 5-20 g |
| Ethanol | 40-80 g |
| Water | ad 100 g |

The active substance is dissolved in ethanol to give a clear solution. After admixture of the propylene glycol-water solution the hydroxypropylcellulose is left to swell up to give a clear gel.

Example B (cream, o/w type)

| Active substance | 0.05-2 g |
|---|---|
| Polyoxyethylene sorbitan ester | 3-10 g |
| Cetyl alcohol | 7-12 g |
| Vaseline, white | 15-35 g |
| Glycerine | 5-15 g |
| Benzoic acid | 0.1-0.3 g |
| Water | ad 100 g |

The active substance is incorporated into the molten fatty phase at about 70°-75°. The glycerine and the emulsifier are admixed with the aqueous benzoic acid solution. The aqueous phase and the fatty phase are homogenized at about 70° and left to cool to room temperature while homogenizing.

Example C (cream, w/o type)

| Active substance | 0.05-2 g |
|---|---|
| Vaseline, white | 20-40 g |
| Wax, white | 5-15 g |
| Paraffin oil, viscous | 10-20 g |
| Glycerine sorbitan fatty acid ester | 5-10 g |
| Benzoic acid | 0.1-0.2 g |
| Water | ad 100 g |

The active substance is incorporated into the molten fatty phase at about 80°. The aqueous benzoic acid solution, which is likewise at about 80°, is admixed with the fatty phase while homogenizing and the emulsion is left to cool to room temperature while homogenizing further.

Example D (salve)

| | |
|---|---|
| Active substance | 0.05–2 g |
| Paraffin, viscous | 30–50 g |
| Vaseline, white | 40–50 g |
| Castor oil, hardened | ad 100 g |

The active substance is incorporated into the fatty phase, which is at about 80°, and the mixture is left to cool to room temperature while stirring.

I claim:

1. Compounds of formula $$\text{Ret-OA} \qquad \text{I}$$

wherein
Ret is the acyl residue of a retinoid carboxylic acid, A is a residue $(-\text{CHR})-\text{CH}_2\text{O})_n\text{R}^1$, $-\text{C}(\text{R}^4)_2\text{OC}(\text{O})\text{R}^3$, $-\text{CH}_2-\text{CH}(\text{OR}^2)\text{CH}_2\text{OR}^2$ or $-\text{CH}(\text{CH}_2\text{OR}^2)_2$;
R is hydrogen or methyl,
$R^1$ is hydrogen, $C_{1-6}$-alkyl or $C_{1-6}$-alkanoyl,
$R^2$ is $C_{1-6}$-alkyl,
$R^3$ is straight chain $C_{1-6}$-alkyl,
$R^4$ is hydrogen, $C_{1-6}$-alkyl or phenyl; n is a whole number of 3–40.

2. The Compound of claim 1, wherein Ret is the acyl residue of a retinoid carboxylic acid of the formula

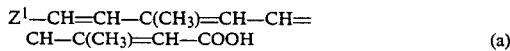

wherein $Z^1$ is a substituted phenyl or cyclohexenyl residue and in which the double bonds in the polyene chain of (a) can have the E- or Z-configuration.

3. The Compound of claim 2, wherein Ret is the acyl residue of all-trans-9-(4-methoxy-2,3,6-trimethylphenyl)-3,7-dimethyl-2,4,6,8-nonatetraenoic acid, of p-[(E)-2-(5,6,7,8-tetrahydro-5,5,8,8-tetramethyl-2-naphthyl)propenyl]benzoic acid, of all-trans-vitamin-A acid or of 13-cis-vitamin-A acid.

4. The Compound of claim 3, wherein Ret is the acyl residue of all-trans-9-(4-methoxy-2,3,6-trimethylphenyl)-3,7-dimethyl-2,4,6,8-nonatetraenoic acid.

5. The Compound of claim 4, wherein A is the residue $(-\text{CHR})-\text{CH}_2\text{O})_n\text{R}^1$.

6. The Compound of claim 5, wherein the compounds is 2-(2-(hydroxyethoxy)ethoxy)ethyl (all-E)-9-(4-methoxy-2,3,6-trimethylphenyl)-3,7-dimethyl-2,4,6,8-nonatetraenoate.

7. The Compound of claim 5, wherein the compounds is 2-(2-(2-(2-Hydroxyethoxy)ethoxy)ethoxy)ethyl (all-E)-9-(4-methoxy-2,3,6-trimethylphenyl)-3,7-dimethyl-2,4,6,8-nonatetraenoate.

8. The Compound of claim 4, wherein A is the residue Polyethylene Glycol.

9. The Compound of claim 8, wherein the compounds is polyethylene glycol(400) mono-(all-E)-9-(4-methoxy-2,3,6-trimethylphenyl)-3,7-dimethyl-2,4,6,8-nonatetraenoate.

10. The Compound of claim 8, wherein the compounds is polyethylene glycol (600)mono-all-E)-9-(4-methoxy or -2,3,6-trimethylphenyl)-3,7-dimethyl-2,4,6,8-nonatetraenoate.

11. The Compound of claim 8, wherein the compounds is polyethyleneglycol(1000) mono-(all-E)-9-(4-methoxy-2,3,6-trimethylphenyl)-3,7-dimethyl-2,4,6,8-nonatetraenoate.

12. The Compound of claim 4, wherein A is the residue $-\text{C}(\text{R}^4)_2\text{OC}(\text{O})\text{R}^3$.

13. The Compound of claim 12, wherein the compounds is methylene acetate (all-E)-9-(4-methoxy-2,3,6-trimethylphenyl)-3,7-dimethyl-2,4,6,8-nonatetraenoate.

14. The Compound of claim 12, wherein the compounds is methylene (all-E)-9-(4-methoxy-2,3,6-trimethylphenyl)-3,7-dimethyl-2,4,6,8-nonatetraenoate pivalate.

15. The Compound of claim 12, wherein the compounds is methylene benzoate (all-E)-9-(4-methoxy-2,3,6-trimethylphenyl)-3,7-dimethyl-2,4,6,8-nonatetraenoate.

16. The Compound of claim 12, wherein the compounds is methylene (all-E)-9-(4-methoxy-2,3,6-trimethylphenyl)-3,7-dimethyl-2,4,6,8-nonatetraenoate 3,4,5-trimethoxybenzoate.

17. The Compound of claim 12, wherein the compounds is methylene o-acetoxybenzoate (all-E)-9-(4-methoxy-2,3,6-trimethylphenyl)-3,7-dimethyl-2,4,6,8-nonatetraenoate.

18. The Compound of claim 12, wherein the compounds is methylene [(2-benzoyl-4-methoxy)phenoxy]acetate (all-E)-9-(4-methoxy-2,3,6-trimethylphenyl)-3,7-dimethyl-2,4,6,8-nonatetraenoate.

19. The Compound of claim 12, wherein the compounds is methylene cinnamate (all-E)-9-(4-methoxy-2,3,6-trimethylphenyl)-3,7-dimethyl-2,4,6,8-nonatetraenoate.

20. The Compound of claim 12, wherein the compounds is methylene p-methoxycinnamate (all-E)-9-(4-methoxy-2,3,6-trimethylphenyl)-3,7-dimethyl-2,4,6,8-nonatetraenoate.

21. The Compound of claim 18, wherein the compounds is 2-(2-(2-(2-hydroxyethoxy)ethoxy)ethoxy)ethyl (all-E)-3,7-dimethyl-9-(2,6,6-trimethyl-1-cyclohexen-1-yl)-2,4,6,8-nonatetraenoate.

22. The Compound of claim 20, wherein the compounds is methylene (all-E)-3,7-dimethyl-9-(2,6,6-trimethyl-1-cyclohexen-1-yl)-2,4,6,8-nonatetraenoate pivalate.

23. The Compound of claim 22, wherein the compounds is 2-(2-(2-(2-hydroxyethoxy)ethoxy)ethoxy)ethyl 3,7-dimethyl-9-(2,6,6-trimethyl-2-cyclohexen-1-yl)-2(Z),4,6,8(E)-nonatetraenoate.

24. The Compound of claim 3, wherein the compounds is ethylidene (ethyl carbonate) (all-E)-9-(4-methoxy-2,3,6-trimethylphenyl)-3,7-dimethyl-2,4,6,8-nonatetraenoate.

25. The Compound of claim 4, wherein compounds is ethylidene benzoate (all-E)-9-(4-methoxy-2,3,6-trimethylphenyl)-3,7-dimethyl-2,4,6,8-nonatetraenoate.

26. The Compound of claim 3, wherein the compounds is ethylidene acetate (all-E)-9-(4-methoxy-2,3,6-trimethylphenyl)-3,7-dimethyl-2,4,6,8-nonatetraenoate.

27. A process for the manufacture of the compounds of claim 1, characterized by reacting a retinoid carboxylic acid of the formula Ret-OH or a reactive derivative thereof with an alcohol of the formula HA or a reactive derivative thereof or a halide of the formula Hal-A, whereby Ret and A have the significance given in claim 1 and Hal is halogen, or reacting a compound of the formula Ret—O—C(R$^4$)$_2$—Hal with a carboxylic acid of formula R$^{31}$COOH, whereby Ret, Hal and R$^4$ have the significance given above and R$^{31}$ is $C_{1-3}$-alkyl, in the presence of a condensation agent and, if desired, functionally modifying reactive groups in the reaction product.

* * * * *

UNITED STATES PATENT AND TRADEMARK OFFICE
CERTIFICATE OF CORRECTION

PATENT NO. : 4,900,478

DATED : February 13, 1990

INVENTOR(S) : Gunter Gross

It is certified that error appears in the above-identified patent and that said Letters Patent is hereby corrected as shown below:

In claim 21, column 16, line 33 delete "18" and insert -- 12 --.

In claim 22, column 16, line 37, delete "20" and insert -- 12 --.

In claim 23, column 16, line 41, delete "22" and insert -- 12 --.

In claim 27, column 16, line 64 delete "$C_{1-3}$" and insert -- $C_{1-6}$ --

Signed and Sealed this

Twelfth Day of February, 1991

*Attest:*

HARRY F. MANBECK, JR.

*Attesting Officer*      *Commissioner of Patents and Trademarks*